United States Patent [19]

Kohn et al.

[11] Patent Number: 4,477,672

[45] Date of Patent: Oct. 16, 1984

[54] ALKYLSULFONYLOXY SUBSTITUTED PHENOXY ALKANOIC ESTERS

[75] Inventors: Gustave K. Kohn, Palo Alto; Joe T. Bamberg, Redwood City, both of Calif.

[73] Assignee: Zoecon Corporation, Palo Alto, Calif.

[21] Appl. No.: 405,853

[22] Filed: Aug. 6, 1982

[51] Int. Cl.$^3$ .................. C07D 213/61; C07D 213/62; C07D 213/64
[52] U.S. Cl. ........................................ 546/294; 71/94; 546/288; 546/296; 546/297; 546/157; 548/166; 548/221; 544/354
[58] Field of Search ................ 546/294, 288, 296, 297

[56] References Cited

U.S. PATENT DOCUMENTS

| | | | |
|---|---|---|---|
| 3,379,752 | 4/1968 | Bolhofer | 560/62 |
| 4,134,751 | 1/1979 | Nishiyama et al. | 71/94 |
| 4,216,007 | 8/1980 | Nishiyama et al. | 71/94 |
| 4,348,221 | 9/1982 | Szczepanski et al. | 71/94 |

*Primary Examiner*—Alan L. Rotman
*Attorney, Agent, or Firm*—Donald W. Erickson; Jacqueline S. Larson

[57] ABSTRACT

3-Alkylsulfonyloxy-4-substituted phenoxy alkanoic acid esters and the use thereof as intermediates for and as herbicides.

5 Claims, No Drawings

ALKYLSULFONYLOXY SUBSTITUTED PHENOXY ALKANOIC ESTERS

This invention relates to novel 3-alkylsulfonyloxy-4-substituted phenoxy alkanoic acid esters which are useful herbicides and intermediates for herbicides.

The novel 3-alkylsulfonyloxy compounds of the present invention are represented by the following formula (A):

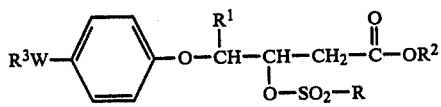

wherein,
R is a primary lower alkyl;
$R^1$ is hydrogen or lower alkyl;
$R^2$ is lower alkyl, lower alkenyl or lower alkynyl;
W is oxygen, sulfur or amino; and
$R^3$ is one of the groups

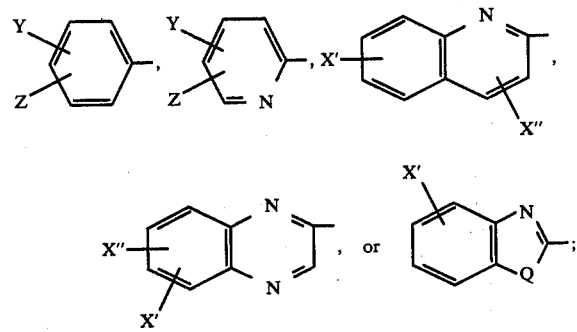

in which,
each of Y and Z is independently selected from hydrogen, lower alkyl, lower haloalkyl, lower alkoxy, lower haloalkoxy, bromo, chloro, fluoro, nitro and cyano;
each of X' and X'' is independently selected from hydrogen, fluoro, chloro, bromo, trifluoromethyl, methoxy or nitro, provided that both X' and X'' cannot be trifluoromethyl, methoxy or nitro; and
Q is oxygen or sulfur.

In the description and claims hereinafter, each of R—$R^3$, Q, W, X', X'', Y and Z is as defined above, unless otherwise specified.

The compounds of formula (A) can be synthesized by the reaction of a lower alkylsulfonyl chloride with a 3-hydroxy compound of formula (I).

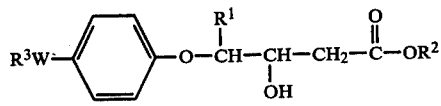

The starting materials of formula (I) can be prepared by methods described by Shy-Fuh Lee, U.S. Pat. No. 4,408,076, the disclosure of which is incorporated herein by reference.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The novel compounds of formulas (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

Into a three neck flask, purged with nitrogen, cooled in an ice water bath, containing ethyl 4-[4-(4-trifluoromethylphenoxy)phenoxy]-3-hydroxypentanoate (2.05 g) in 20 ml of hexane/benzene (1:1) is added slowly mesyl chloride (0.65 g, 1.1 equiv.) in 10 ml of hexane/benzene (1:1) and trimethylamine (0.67 g, 1.3 equiv) in 10 ml of hexane/benzene (1:1) at 0°. The reaction mixture is stirred for about one hour. Then the mixture is worked up by addition of methylene chloride and dilute acetic acid and partitioning with ice water. The organic phase is dried over magnesium sulfate, filtered and evaporated under vacuum to yield ethyl 4-[4-(4-trifluoromethylphenoxy)phenoxy]-3-methanesulfonyloxypentanoate, an oil, which can be purified by column chromatography, silica gel, eluting with hexane/ethyl acetate (4:1). Two diastereoisomers are separable from the thus-obtained compound by use of prep. thin layer chromatography using ethylacetate/hexane (15:85) solvent.

The foregoing procedure is repeated using ethanesulfonyl chloride in place of mesyl chloride to yield ethyl 4-[4-(4-trifluoromethylphenoxy)phenoxy]-3-ethanesulfonyloxypentanoate.

EXAMPLE 2

Each of the 3-hydroxy compounds under Table 1 is reacted with mesyl chloride using the process of Example 1 to yield the corresponding 3-mesylate.

TABLE 1

(1) Ethyl 4-[4-(5-trifluoromethyl-2-pyridyloxy)phenoxy]-3-hydroxypentanoate.
(2) Ethyl 4-[4-(3-chloro-5-trifluoromethyl-2-pyridyloxy)phenoxy]-3-hydroxypentanoate.
(3) Ethyl 4-[4-(3,5-dichloro-2-pyridyloxy)phenoxy]-3-hydroxypentanoate.
(4) Methyl 4-[4-(2-chloro-4-trifluoromethylphenoxy)phenoxy]-3-hydroxypentanoate.

In addition to the herbicidal activity described herein of the compounds of the present invention, the compounds are useful intermediates for the synthesis of 3-thiols and 3-thioethers of formula (B). Thus, for example, reaction of a 3-mesylate of the present invention with a mercaptide (such as methyl mercaptan with sodium hydride or potassium hydride) in an organic solvent provides compounds of formula (B). 3-Thiols of formula (B) can be prepared by reaction of a compound of formula (A) with sodium hydrosulfide in an organic solvent such as an alcohol.

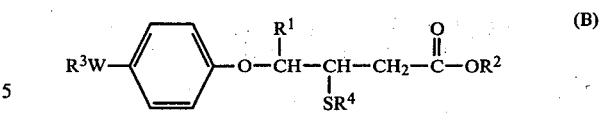

In the above formula $R^4$ is hydrogen or lower alkyl.

The compounds of formula (B) are useful for the control of weeds in the same manner as described herein for the compounds of formula (A).

Grass weeds on which the compounds of formulas (A) and (B) can be used as herbicides include green foxtail, watergrass, shattercane and Johnsongrass.

What is claimed is:

1. A compound of the following formula:

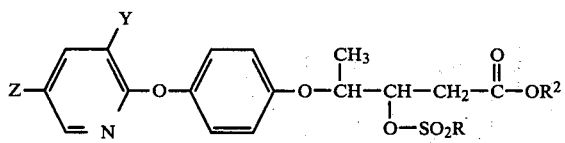

wherein,
R is a primary lower alkyl;
$R^2$ is lower alkyl; and
each of Y and Z is independently selected from hydrogen, lower alkyl, lower haloalkyl, lower alkoxy, lower haloalkoxy, bromo, chloro, fluoro, nitro and cyano.

2. A compound according to claim 1 wherein each of Y and Z is chloro and R is methyl.

3. A compound according to claim 1 wherein Z is trifluoromethyl and R is methyl.

4. The compound according to claim 3 wherein Y is chloro and $R^2$ is ethyl.

5. The compound according to claim 3 wherein Y is hydrogen and $R^2$ is ethyl.

* * * * *